United States Patent
Medasani

(10) Patent No.: US 8,496,977 B2
(45) Date of Patent: Jul. 30, 2013

(54) **NATURAL EXTRACT FROM WHOLE BANANA FRUIT (*MUSA* SPP)**

(76) Inventor: Munisekhar Medasani, Hyderabad (IN)

( * ) Notice: Subject to any disclaimer, the term of this patent is extended or adjusted under 35 U.S.C. 154(b) by 0 days.

(21) Appl. No.: 13/389,998

(22) PCT Filed: Aug. 11, 2010

(86) PCT No.: PCT/IB2010/001994
§ 371 (c)(1),
(2), (4) Date: Apr. 27, 2012

(87) PCT Pub. No.: WO2011/018700
PCT Pub. Date: Feb. 17, 2011

(65) Prior Publication Data
US 2012/0219510 A1    Aug. 30, 2012

(30) Foreign Application Priority Data
Aug. 12, 2009 (IN) .......................... 1916/CHE/2009

(51) Int. Cl.
*A61K 36/00* (2006.01)
*A61K 9/68* (2006.01)
*A61K 33/42* (2006.01)

(52) U.S. Cl.
USPC .............................. 424/725; 424/48; 424/601

(58) Field of Classification Search
None
See application file for complete search history.

(56) References Cited

U.S. PATENT DOCUMENTS

| | | | |
|---|---|---|---|
| 3,974,301 A | 8/1976 | Luh et al. | |
| 4,273,792 A | 6/1981 | Johnson et al. | |
| 4,874,617 A | 10/1989 | Sole | |
| 4,921,709 A | 5/1990 | Solé | |
| RE34,237 E | 4/1993 | Sole | |
| 5,470,879 A | 11/1995 | Sauvaire et al. | |
| 5,972,344 A | 10/1999 | Edwards | |
| 5,989,559 A | 11/1999 | Edwards | |
| 6,013,260 A * | 1/2000 | Edwards | 424/777 |
| 6,753,019 B1 | 6/2004 | Lang et al. | |
| 7,098,029 B1 | 8/2006 | Belyea et al. | |

FOREIGN PATENT DOCUMENTS

| | | |
|---|---|---|
| CN | 101228942 A | 7/2008 |
| JP | 03056424 A * | 3/1991 |
| JP | A-2005-306780 | 11/2005 |
| WO | WO 2005/115423 A1 | 12/2005 |

OTHER PUBLICATIONS

Silva et al, Physiochemical and sensory quality of spirits made from banana pulp and whole banana after enzymic hydrolysis, Alimentos e Nutricao (2009), 20(2), 217-221.*

Feldman et al, Catecholamine and serotonin content of foods: effect on urinary excretion of homovanillic and 5 hydroxyindoleacetic acid. Journal of the American Dietetic Association, Aug. 1987. vol. 87, No. 8. p. 1031-1035.*

Emaga et al, Effects of the stage of maturation and varieties on the chemical composition of banana and plantain peels. Food Chemistry (2007), 103(2), 590-600.*

Deka et al, Variation in biochemical constituents of banana fruit cv. Borjahaji (AAA) at different stages of development. Annals of Agri Bio Research (1997) vol. 2, No. 1, pp. 71-75.*

Cordenunsi et al, Non-starch polysaccharide composition of two cultivars of banana (*Musa acuminata* L.: cvs Mysore and Nanic Do) Carbohydrate polymers, Jan. 5, 2008 vol. 71, issue 1 p. 26-31.*

Vijayakumar et al., "Antioxidant Activity of Banana Flavonoids," *Fitoterapia*, 2008, pp. 279-282, vol. 79, Elsevier B.V.

Tressl et al., "Biogenesis of Banana Volatiles," *Journal of Agricultural Food Chemistry*, 1973, pp. 560-565, vol. 21—No. 4.

Dominguez-Puigjaner et al., "Differential Protein Accumulation in Banana Fruit during Ripening," *Plant Physiology*, 1992, pp. 157-162, vol. 98.

Kanazawa et al., "High Content of Dopamine, a Strong Antioxidant, in Cavendish Banana," *Journal of Agricultural Food Chemistry*, 2000, pp. 844-848, vol. 48, American Chemical Society.

MacNaughton et al., "A Role for Dopamine as an Endogenous Protective Factor in the Rat Stomach," *Gastroenterology*, 1989, pp. 972-980, vol. 96, American Gastroenterological Association.

Abstract of Alanko et al., "Effects of Catecholamines on Eicosanoid Synthesis with Special Reference to Prostanoid/Leukotriene Ratio," *Free Radical Biology and Medicine*, 1992, pp. 677-688, vol. 13—No. 6.

Badria, "Melatonin, Serotonin, and Tryptamine in Some Egyptian Food and Medicinal Plants," *Journal of Medicinal Food*, 2002, pp. 153-157, vol. 5—No. 3, Mary Ann Liebert, Inc.

Peumans et al., "Fruit-Specific Lectins from Banana and Plantain," *Planta*, 2000, pp. 546-554, vol. 211, Springer-Verlag.

Jun. 2002, "Burn Fat Like Never Before: The Intense Fat-Burning Power of New Hydroxycut can Help get you Shredded to the Bone!-BodyBuilding Supplement," www.findarticles.com/p/articles/mi_m0KFY/is_4_20/ai_98464596/pg_2, Retrieved May 31, 2012.

Excerpts of Kandaswami, "Chapter 30: The Role of Tea in Weight Management," *Epidemiology, Pathophysiology and Prevention*, 2007, www.crcnetbase.com, Retrieved Jun. 1, 2012.

Preston et al., *Handbook of Clinical Psychopharmacology for Therapists*, 2010, pp. 35-37.

Jan. 20, 2011 International Search Report issued in International Application No. PCT/IB2010/001994.

* cited by examiner

*Primary Examiner* — Qiuwen Mi
(74) *Attorney, Agent, or Firm* — Oliff & Berridge, PLC

(57) ABSTRACT

A natural Extract from whole Fruit of Banana (*Musa* Spp.), (including edible portion and peel), whether unripe or ripe, containing mainly natural Melatonin, Serotonin, Catecholamines and its precursors; amino acids tryptophan and tyrosine; minerals potassium, magnesium, phosphorous and antioxidants. The extract contains very minimal or no carbohydrates.

19 Claims, No Drawings

NATURAL EXTRACT FROM WHOLE BANANA FRUIT (*MUSA* SPP)

BACKGROUND

Banana is the common name for the fruit of herbaceous plant of the family *Musaceae* and genus *Musa*. They are native to the tropical region of Southeast Asia. Bananas are mostly cultivated for the fruit and to also for fiber and ornamental use.

About 170 countries produce bananas in the world. In the developing world banana are considered as staple food. It provides instant energy, rich source of fiber, minerals and vitamins. It has about 200 volatile components which include phyto-nutrients, sterols and fatty acids.

Bananas along with a glass of whole milk are considered as staple food and provide the entire nutrient requirement for the body. This is considered as most preferred diet for dieters. Being rich source of neurotransmitter and its precursors, it provides instant mood elevation. Potassium rich bananas are good for hypertensive people. This is the only fruit considered very safe from infants to the old ago people.

Traditionally it is considered good for any gastric irritations, ulcers, constipation. Its starch provides a protective layer in the stomach while its non-digestible fiber is good for cholesterol lowering and constipation. Native Africans use inner part of banana peel for insect bites and skin problems. In Ayurveda they suggest eating of banana peel for diabetics as it is good source of potassium, but do not contain sugars which are more in the edible portion.

Ancient uses and recent studies have shown that bananas have good antioxidant properties and correcting electrolyte imbalance.

Drugs used for antidepressant and anti-anxiety treatment mainly falls into two classes i.e. Serotonin-norepinephrine reuptake inhibitors (SNRIs) and Selective serotonin reuptake inhibitors/serotonin-specific reuptake inhibitor (SSRIs). These drugs work by inhibiting the reuptake of the neurotransmitters serotonin and norepinephrine. This results in an increase in the extracellular concentrations of serotonin and norepinephrine and therefore an increase in neurotransmission.

DESCRIPTION OF THE INVENTION

For the convenierlhe of readers it is understood that wherever the word 'extract' mentioned in the context of invention, it refers to the extract claimed under this invention. Wherever the word 'inventor' is mentioned in the) context of this invention, it refers to the inventor named in this patent application.

All the traditional uses and latest inventions have used either edible portion of banana or peel for separation of flavonoids, phenols and volatile compounds. Inventor himself applied for patents earlier for separation of natural potassium from bananas.

Inventor's search on literature has revealed mainly powders, puree, syrups and juices of banana. Banana Powers contains carbohydrates more than 80%. Banana puree is mainly made out of edible portion of banana and used for infant food and deserts. Banana juice is mainly made of edible portion of banana and contains natural sugars. There are some research articles on preparation of banana wine by using enzymatic process and converting sugars into alcohol by using yeast fermentation. Banana lectins are being used mainly for research purpose. Banana essence is being isolated from peels of banana, which is mainly as food additive and fragrance. Insoluble banana fiber, banana starch and banana pectin is being isolated and being used different industrial purposes.

Present invention is for whole fruit extract of banana, which includes edible portion of fruit and peel, with physical treatment, enzymatic process and resin treatment. This innovation is for separation of Nitrogen containing molecules like, but not limited to, amino acids, proteins, glyco-proteins, neurotransmitters and its precursors, minerals. This extract is characterized by very minimal or not containing simple sugars and fiber.

Innovation and novelty is specific extraction whole banana fruit which mainly containing neurotransmitter, minerals and Nitrogen containing molecules like amino acids, proteins, glyco-proteins and antioxidants. This pure and specific extract of banana is effective for human consumption at as little as 100 mg per dose, as this extract's bioavailability of above nutrients is higher compared to eating whole banina and nontoxic at even 1,000 mg per dose.

Besides providing extract with good antioxidant properties, inventor has taken care of retaining natural Norepinephrine and Epinephrine in the extract which is known for increasing body thermogenesis and energy expenditure by burning body fat. Norepinephrine and epinephrine are the constituents in the Green Tea which are believed to have fat burning capability. Dopamine also retained in the extract. Dopamine is known for mood elevation and for erectile dysfunction. Combination of dopamine and norepinephrine are know to increase the energy levels of the body, by increasing the respiration at mitochondria level and also causing mood elevation and motivation. Another surprising result the inventor has found is, this extract is causing thermogenesis whereby it improves cold adoption and subjects are able to withstand for sudden cold exposure.

As far as the information available to the inventor at this time, it is not known to the art to extract whole banana fruit extract which is rich in catecholarnines, antioxidants, minerals and micronutrients which are good for model elevation, destressing properties, has considerable antioxidant properties, takes care of sleeping disorders and burns body fat by increasing thermogenesis. This extract can be provided for usage in simple pill form which provides goodness of peel and edible portion. Thus, this invention provides a natural remedy for all the above human sufferings by a single natural extract without need to load the body with excess sugars, carbohydrates and fibers.

Human body maintains levels of dopamine, servionin, norepinephrine in the brain through blood-brain-barrier (BBB) function. For example, intake of dopamine is converted into L-Dopa, then transported into brain, then reconverted into dopamine. With this BBB function, human body avoids any excess inflow of neurotransmitters into brain. Instead of interfering with the body's natural function, like SSRI and SNRI, it is advised in wholistic and traditional medicine that you provide what is required by the body and it knows how to regular the system. This extract provides that natural relief without interfering with the body natural functions.

This extract provides the similar result like antidepressants i.e. increasing levels of neurotransmitters naturally in the body whereby providing similar effect as SSRIs and SNRis naturally. This extract is water soluble; hence body will utilize required neurotransmitters and eliminates the excess through excretion. Oral and cytotoxicity tests conducted has shown that the extract is safe even at higher doses.

It is also understood that a standardized extract with particular level of minerals or neurotransmitters can be made from this extract or natural neurotransmitters can be isolated and standardized from this process or extract. It is understood and claimed that this kind of standardization falls under scope of this invention.

It is well known that about 30% of the banana produce get wasted in the processing and transporting anywhere in the world. Some of it goes as feed to animals, but most do not. This invention provides a scope to banana farmers to process damaged bananas into a value added product, which will have national and international importance.

Process propose in the claims differs mainly in 3 aspects i.e. having minimal or no simple sugars, having minimal or no insoluble fiber, having higher percentage of neurotransmitters (w/w) when converted into powder foam. These three additional features together make the claimed extract as novel and innovative.

Inventor himself filed an earlier patent for saturation of body stores with natural potassium extracted from bananas. This earlier patent has been abandoned now, as present invention supersedes the benefits of earlier invention in many ways.

It is also known and understood that proposed treatment with charged ion exchange resins is being used in juices/syrups/puree manufacturing for clarification of juices/syrups/puree and removing minerals, proteins etc. But constituents which collected into resin never lied been used for purpose discussed or claimed in this invention. It may be understood that because only edible portion of banana is used for making juices/syrups/puree. Constituents recovered from resins in juices/syrups/puree manufacturing industry also falls under the scope of this invention even though those are recovered only from edible portion of the fruit or whole fruit.

Patent References
1. U.S. Pat. No. 5,989,551 Banana peel extract composition and method for extraction
2. U.S. Pat. No. 4,273,792 Banana Processing
3. U.S. Pat. No. 4,874,617 Banana Processing
4. U.S. Pat. No. 3,974,301 Dehydrated banana product
5. U.S. Pat. No. 4,921,709 Banana peel processing
6. U.S. Pat. No. 6,013,260 Banana peel extract composition and method for extraction for TOPICAL MEDICINE
7. U.S. Pat. No. 6,753,019 Food supplement
8. U.S. Pat. No. 7,098,029 Product and method for control of obesity
9. U.S. Pat. No. 5,470,879—Treatment of non-insulin-dependent diabetes
10. U.S. RE34237 Banana processing Non-Patent References
1. The antioxidant activity of flavonoids from banana (*Musa paradisiaca*) was studied in rats fed normal as well as high fat diets. Concentrations of peroxidation products namely malondialdehyde, hydroperoxides and conjugated diens were significantly decreased whereas the activities of catalase and superoxide dismutase were enhanced significantly. Concentrations of glutathione were also elevated in the treated animals. (Antioxidant activity of banana flavonoids S. Vijayakumar et al./Fitoterapia 79 (2008) 279-282)
2. Over 150 volatile compounds have been identified in bananas by various investigators. Most of the corn vents are aliphatic esters, alcohols, and carbonyls. (BIOGENESIS OF BANANA VOLATILES J. Ager. FoodChem., Vol. 21, No. 4, 1973)
3. Banana (*Musa acuminata*, cv Dwarf Cavendish) proteins were extracted from pulp tissue at different stages of ripening and analyzed by two-dimensional electrophoresis. The results provide evidence of differential protein accumulation during ripening. Two sets of polypeptides have been detected that increase substantially in ripe fruit. These polypeptides were characterized as glycoproteins by western blotting and concanavalin A binding assays. (Differential Protein Accumulation in Banana Fruit during Ripening, Plant Physiol. (1992) 98, 57-162)
4. The present study revealed that banana contained a strong antioxidant, dopamine, in large amounts. the antioxidative potency of dopamine was greater than that of BHA, BHT, flavonoids, glutathione, and catechin, and similar to that of the strong antioxidants gallocatechin gallate and ascorbic acid. (Banana Antioxidant *J. Agric, Food Chem.*, Vol. 48, No. 3, 2000)
5. Dopamine has been found to protect against intestinal mucosal injury by modulating eicosanoid synthesis (MacNaughton and Wallace, 1989; Alanko et al, 1992).
6. The results of this screening showed that the pulp of underripe and ripe yellow banana contains 5-hydrokytryptamine at concentrations of 31.4 and 18.5 ng/g, respectively. The average amounts of melatonin in 100 g of fruit or vegetable tissue were as follows: banana, 47 ng. (Melatonin, Serotonin, and Tryptamine in Some Egyptian Food and Medicinal Plants, JOURNAL OF MEDICINAL FOOD Volume 5, Number 3, 2002)
7. The Presence of relatively large quantities of mannose-specific jacalin-related lectins in ripe banana and plantain fruits raises the question of the physiological role of these ruite-associated biological active proteins. (Banana and Plantain fruit lectins, Planta (2000) 211:546-554)
8. Dopamine had a faster radical-scavenging rate than catechin and was similar to gallocatechin gallate. Ascorbic acid is the strongest water-soluble antioxidant. Dopamine exhibited similar activity to ascorbic acid. Based on ripening stage bananas contain 8-118 mg/100 g of Peel and 0.8-2.10 mg/100 g of Pulp. (High Content of Dopamine, a Strong Antioxidant, in Cavendish Banana *J. Agric. Food Chem.* 2000, 48, 844-848)
9. the researchers found that the green tea group burned 35 percent more fat than the group not taking it. Measures of norepinephrine also went up 37 percent! Green tea is thought to work by preventing the breakdown of norepinephrine in the body, which results in higher levels of uorepinephrine available to do its fat-burning work. (http://findarticles.com/p/articles/mi m0KFY/is 4 20/ai 98464596/pg 2/)
10. Catecholamine hormones such as norepinephrine and epinephrine can increase therogenesis and lipolysis, ding to increase energy expenditure and decreased fat stores. (The Role of Tea in Weight Management)
11. Nerve cells in the three critical neurotransmitter systems (dopamine, serotonin, and norepinephrine) in the total represent less than 1 of these systems can result in marked dysregulation of the brain, and at -times, in catastrpic psychiatric symptoms. At other times, the impact is greater and more long-lasting, but it is also subject to eventual spontaneous remission, as is the case in some types of major depression. (Handbook of clinical psychopharmacology for therapists By John Preston, John H. O'Neal, Mary C. Talaga)

What is claimed:

1. An extract from a whole fruit of a banana including edible portion and peel, whether unripe or ripe, containing mainly neurotransmitters and their precursors, amino acids, minerals, and antioxidants: wherein the minerals comprise potassium, magnesium, and phosphorous;

the extract contains very minimal or no carbohydrates;

mineral content in the extract is between 20 and 80% of weight: and carbohydrates in the extract are between 0.05 and 30% of weight.

2. The extract as claimed in claim 1, wherein the extract contains neurotransmitters including serotonin, melatonin, dopamine, norepinephrine, epinephrine or its oxidized forms.

3. The extract as claimed in claim 1, wherein pH of the extract is between 4 to 7.

4. The extract as claimed in claim 1, wherein simple sugars in the extract are less than 10% of weight.

5. The extract as claimed in claim 1, wherein starch, fiber and pectin together in the extract is less than 20% of weight.

6. The extract as claimed in claim 1, wherein the extract is soluble in water.

7. The extract as claimed in claim 1, wherein the extract is in powder form with less than 15% moisture content.

8. The extract as claimed in claim 1, wherein the extract is in powder, gel, paste, semi-solid, or liquid forms.

9. The extract as claimed in claim 1, wherein the extract is a food supplement; medicine; food additive; adjuvant; or an adjuvant to food supplements or foods or drinks or drink mixes or medicines.

10. The extract as claimed in claim 1, wherein the extract is administered to mammals and animals by orally, subcutaneously, nasally, transdermally, dermally, sublingually or being in the form of nanoparticles or nano gels or adsorbed on an excipient.

11. The extract as claimed in claim 1, wherein the extract is formulated as a tablet, caplet, capsule, patch, softgel, topical gel, drink, powder, effervescent, drink mix, chewable, chewing gum, or gummy tablet for administering to mammals and animals.

12. The extract as claimed in claim 11, wherein the extract further comprises other plant or animal extracts, minerals, vitamins, proteins, amino acids, fatty acids, antioxidants, flavors, taste enhancers, binding agents, preservatives and adjuvants for increased activity, taste, flavour, shelf life, or efficacy.

13. The extract as claimed in claim 1, wherein the extract is used for mammals and animals, in one or more of conditions, for mood elevation, reducing stress, anxiety and depression; increasing Basal Metabolism Rate (BMR), thermogenesis, obesity, hyperlipidemia, hypercholesterol, hypertension, diabetes, sleeping disorders, neurological disorder, muscular disorder, erectile dysfunction and to increase potassium content in the body.

14. The extract as claimed in claim 1, wherein a protein, a nitrogen-containing compound, and the minerals, neurotransmitters, and amino acids are recovered by using cation resins and are for mammal and animal use as medicines, food supplement, adjuvant or additive.

15. The extract as claimed in claim 1, wherein the extract is for mammals and animal use at doses 1 to 1,000 mg in powder or equivalent to powder per day.

16. The extract as claimed in claim 1, wherein a protein, a nitrogen-containing compound, and the minerals, neurotransmitters, and amino acids are obtained using cation resins from a process line using cation resins in a fruit juice industry.

17. An extract from a whole fruit of a banana including edible portion and peel, whether unripe or ripe, containing mainly melatonin, serotonin, catecholamines and its precursors; amino acids tryptophan and tyrosine; minerals potassium, magnesium, phosphorous and antioxidants, wherein the extract contains very minimal or no carbohydrates; and the extract is obtained by cleaning and disinfecting of at least one whole banana;

cutting and mashing the whole banana into paste and mixing with a required quantity of water;

cooking the paste and water mixture at temperatures above 75° C. to break down fiber and starches;

treating fiber, starch, and pectin with enzymes including cellulase enzymes, amylase enzymes, amylose, amylopectin, and pectinase enzymes for breaking down and digesting fiber, starch and pectin;

passing the above treated liquid through a charged ion exchange resin for collecting or recovering minerals, neurotransmitters, proteins, amino acids, and nitrogen containing compounds;

recovering and collecting the above constituents from the ion exchange resin by treating with organic or inorganic pH adjusted liquids;

evaporation of liquid under vacuum below 70° C. to reduce water content;

drying the reduced water content liquid into a powder by using a member selected from the group consisting of spray drying, drum dryer, short path distillation, lyophilization, and film evaporators;

grinding and sieving the powder to make a fine powder; and adding an additive selected from the group consisting of antioxidants, preservatives, and caking agents.

18. A process of obtaining the extract according to claim 1, the process comprising:

cleaning and disinfecting of at least one whole banana;

cutting and mashing the whole banana into paste and mixing with a required quantity of water;

cooking the paste and water mixture at temperatures above 75° C. to break down fiber and starches;

treating fiber, starch and pectin with enzymes including cellulase enzymes, amylase enzymes, amylose, amylopectin, and pectinase enzymes for breaking down and digesting fiber, starch and pectin;

passing the above treated liquid through a charged ion exchange resin for collecting or recovering minerals, neurotransmitters, proteins, amino acids, and nitrogen containing compounds;

recovering and collecting the above constituents from the ion exchange resin by treating with organic or inorganic pH adjusted liquids;

evaporation of liquid under vacuum below 70° C. to reduce water content;

drying the reduced water content liquid into a powder by using a member selected from the group consisting of spray drying, drum dryer, short path distillation, lyophilization, and film evaporators;

grinding and sieving the powder to make a fine powder; and adding an additive selected from the group consisting of antioxidants, preservatives, and caking agents.

19. The method as claimed in claim 18, wherein the minerals, neurotransmitters, proteins, amino acids and nitrogen containing compounds are recovered by using a process including a component selected from the group consisting of HPLC, gel columns, decanters, centrifuges, and pressure filters.

* * * * *